(12) United States Patent
Carpay et al.

(10) Patent No.: US 6,383,748 B1
(45) Date of Patent: *May 7, 2002

(54) ANALYTICAL TEST DEVICE WITH SUBSTRATE HAVING ORIENTED THROUGH GOING CHANNELS AND IMPROVED METHODS AND APPARATUS FOR USING SAME

(75) Inventors: Wilhemus M. Carpay, Liempde (NL); Roeland F. Papen, Guilford, CT (US)

(73) Assignee: Pamgene B.V. (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 103 days.

(21) Appl. No.: 09/395,514

(22) Filed: Sep. 14, 1999

(51) Int. Cl.$^7$ .................................................. C12Q 1/68
(52) U.S. Cl. ............................ 435/6; 436/518; 436/538; 436/528; 436/165; 436/810; 436/805; 422/58; 422/57; 422/101; 435/530; 435/970; 435/973; 435/287.1; 435/287.2
(58) Field of Search ............................ 435/6, 970, 973, 435/287.1, 287.2; 436/518, 538, 528, 165, 810, 805, 530; 422/58, 57, 101

(56) References Cited

U.S. PATENT DOCUMENTS

| | | | |
|---|---|---|---|
| 4,427,415 A | | 1/1984 | Cleveland |
| 4,777,021 A | | 10/1988 | Wertz et al. |
| 4,797,259 A | * | 1/1989 | Matkovich et al. |
| 5,188,733 A | * | 2/1993 | Wang et al. |
| 5,234,594 A | * | 8/1993 | Tonucci et al. |
| 5,234,840 A | * | 8/1993 | Appleton |
| 5,843,767 A | * | 12/1998 | Beattie |
| 6,017,698 A | * | 1/2000 | Bienhaus et al. |
| 6,017,767 A | * | 1/2000 | Chandler |

FOREIGN PATENT DOCUMENTS

| | | |
|---|---|---|
| EP | 0 178 831 B1 | 7/1991 |
| WO | WO 99/02266 | 1/1999 |

OTHER PUBLICATIONS

Rigby et al., "An Anodizing Process for the Production of Inorganic Microfiltration Membranes," Trans. Inst. Metal Finish, 1990, vol. 68, (3), pp. 95–98.

* cited by examiner

Primary Examiner—Bao-Thuy L. Nguyen
(74) Attorney, Agent, or Firm—Knoble & Yoshida LLC

(57) ABSTRACT

The present invention is directed to methods for analyzing one or more fluid samples for the presence, amount or identity of one or more analytes optionally present in said samples, which uses a device having one or more round wells with a fixed diameter, the wells exposing a substrate of a specific thickness, whereby the substrate has oriented through going channels, in the area of the substrate exposed in the well is provided with at least one binding substance specific for a least one of said analytes. Using the device the sample fluid is forced to pass through the channels in the substrate from the upper side of the substrate to the lower side of the substrate and back at least one time, under conditions that are favorable to a reaction between any analyte present in the sample and the binding substances.

12 Claims, 4 Drawing Sheets

Product Characteristics.

- Samplesize should also be limited such that sample cannot come off because of its weight.

Fluidics control

Reversing the pressure will reverse the process...

...and ultimately the droplet is again on top of the membrane.

Product Characteristics.

- Samplesize should also be limited such that sample cannot come off because of its weight.

$$V_{max,2} = \pi \cdot R_{well}\left(\frac{2\cdot \gamma}{\rho \cdot g} + R_{well}\cdot d\right)$$

ANALYTICAL TEST DEVICE WITH SUBSTRATE HAVING ORIENTED THROUGH GOING CHANNELS AND IMPROVED METHODS AND APPARATUS FOR USING SAME

FIELD OF THE INVENTION

The present invention relates to a device for performing an assay, which device comprises a substrate having oriented through-going channels, said channels opening out on a surface for sample application, the channels in at least one area of the surface for sample application being provided with a first binding substance capable of binding to an analyte.

BACKGROUND OF THE INVENTION

Such a device is disclosed in WO95/11755 for "sequencing by hybridization" applications. The device comprises a substrate provided with channels, the channels being oriented substantially perpendicular to the surface of the substrate. Three types of substrate are disclosed. The first type is comprised of a multitude of hollow glass fibers. It is manufactured by stacking glass fibers having an etchable core, providing the stack with flat ends, polishing those ends, and etching the cores, usually with acid. The second type of substrate is produced by electrochemical etching of a crystalline silicon wafer. First, the position of the channels as well as their size are defined using standard photolithographic methods. Subsequently the oriented channels are formed electrochemically. The third type of substrate is produced by nuclear track etching of an inorganic substrate. This method, comprising the steps of exposing the substrate to heavy, energetic charged particles and wet-etching, results in a substrate with channels scattered randomly over the surface of the substrate. With higher pore densities and porosity there is more chance of fusion of channels, which show reduced flow resistance with respect to other, non-fused channels.

All three types of substrates are quite expensive because of the labor-intensive manufacturing processes and/or expensive starting materials and wasteful operations, such as sawing and polishing, and/or expensive equipment. In addition, the substrates are characterized by a relatively low porosity of 30% and less. More advantageous, higher porosities of up to 80% are said to be achievable, but only at relatively low channel densities, with the disadvantage that the effective surface area of the channels of a particular area of the substrate is lower in comparison with a substrate having a comparable porosity but with higher channel densities (and consequently narrower channels). The silicon-based substrates as disclosed in WO 95/11755 are not transparent for light. These substrates therefore deteriorate the advantageous use of optical marker systems for the detection of analyte bound in the substrate. Popular optical marker systems are for instance based on enzymatically induced color reactions, on bio- or chemi-luminescence, or on photoluminescence. In the latter case both the excitation light and emitted luminescent light have to pass through the substrate material.

Another device comprising a substrate with through-going oriented channels is described in co-pending application number EP98104938, the contents of which are herewith incorporated by reference.

In EP98/04938 a device is disclosed wherein the porous substrate is an electrochemically manufactured metal oxide membrane.

Metal oxide membranes having through-going, oriented channels can be manufactured cheaply through electrochemical etching of a metal sheet. Metals considered are, among others, tantalum, titanium, and aluminium, as well as alloys of two or more metals and doped metals and alloys. The metal oxide membranes are transparent, especially if wet, which allows for assays using various optical techniques. Such membranes have oriented channels with well controlled diameter and advantageous chemical surface properties. When used in an assay the channels in at least one area of the surface of the electrochemically manufactured metal oxide membrane are provided with a first binding substance capable of binding to an analyte. According to a preferred embodiment the metal oxide membrane is comprised of aluminium oxide.

Therefore aluminium oxide membranes may accommodate for high densities of areas comprising different first binding substances. Aluminium oxide membranes having oriented through-going channels are disclosed by Rigby, W. R. et al. (Trans. Inst. Metal Finish., 68(3), p. 95, 1990).These membranes were used to purify viruses, and to store enzymes for sensor purposes, and, as disclosed in EP98/04938 were found to be highly suitable as substrates in, flow trough devices for, for example, probe-based assays. Reagents used in these assay are immobilized in the channels of the substrate and the sample fluid will be forced trough the channels to be contacted with the reagents.

In WO87/07954 a modification of so called manifold vacuum devices is described: The permeability of the base of the wells in, for example, a 96-well microtiter plate, is used to improve the mixing of fluid in the wells, by repeatedly applying a pressure difference over the porous base of the well and thus forcing the fluid to pass trough the base and, subsequently, back into the well. It was shown that this procedure results in a better mixing of the ingredients (for example, beads, microspheres or other entities of the small fluid sample in the wells) and is thus an alternative for mechanical mixing methods like bubbling, vortexing stirring or agitating the sample fluid by swirling the plate.

For example, as described in WO87/07954 antigen bound glass fibers were formed into a filter and used as a basis in the wells of a manifold plate. An enzyme immunoassay is performed whereby a highly visible purple precipitate is formed that is of large enough size to be trapped by the filter.

SUMMARY OF THE INVENTION

The object of the present invention is to provide optimized methods of contacting a flow trough device comprising a substrate having oriented troughgoing channels with the sample fluid. Thus, the present invention provides new and non-obvious ways of performing an assay using flow trough devices with oriented trough going channels in which reagents have been immobilized. Use is made of the capillary forces of the channels in the substrate. Based on the dimensions of the substrate and the device wherein it is used an optimal method of contacting the sample fluid with the reagents in the channels is provided.

With the present invention it has been found that based on the physical parameters of the substrate, the device and the sample volume, a very efficient and sensitive method for analyzing sample fluids can be provided.

Thus, the present invention is concerned with a method for analyzing one or more fluid samples for the presence, amount or identity of one or more analytes optionally present in said samples, said method comprising the steps of:

(a) providing a device comprising one or more round wells with a fixed diameter, said wells exposing a substrate of a specific thickness, said substrate having oriented trough going channels, and the area of the substrate exposed in the well being provided with at least one binding substance specific for at least one of said analytes, (b) adding an amount of sample fluid to one or more of the wells of the device, the amount of added sample fluid being calculated on the basis of the dimensions of the wells and the substrate, (c) generating an alternating flow trough the substrate in the wells whereby the liquid volume of sample fluid is forced to pass trough the channels in the substrate from the upper side of the substrate to the lower side of the substrate and back at least one time, under conditions that are favorable to a reaction between any analyte present in the sample and the binding substance(s), (d) reading any signal generated in any of the wells and (e) determining from said signal(s) the presence, amount and/or identity of said one or more analytes.

If necessary (for example, in case of an assay where a bound-free separation step is required, the substrate can be washed prior to reading the signal.

DETAILED DESCRIPTION OF THE INVENTION

Figure 1:
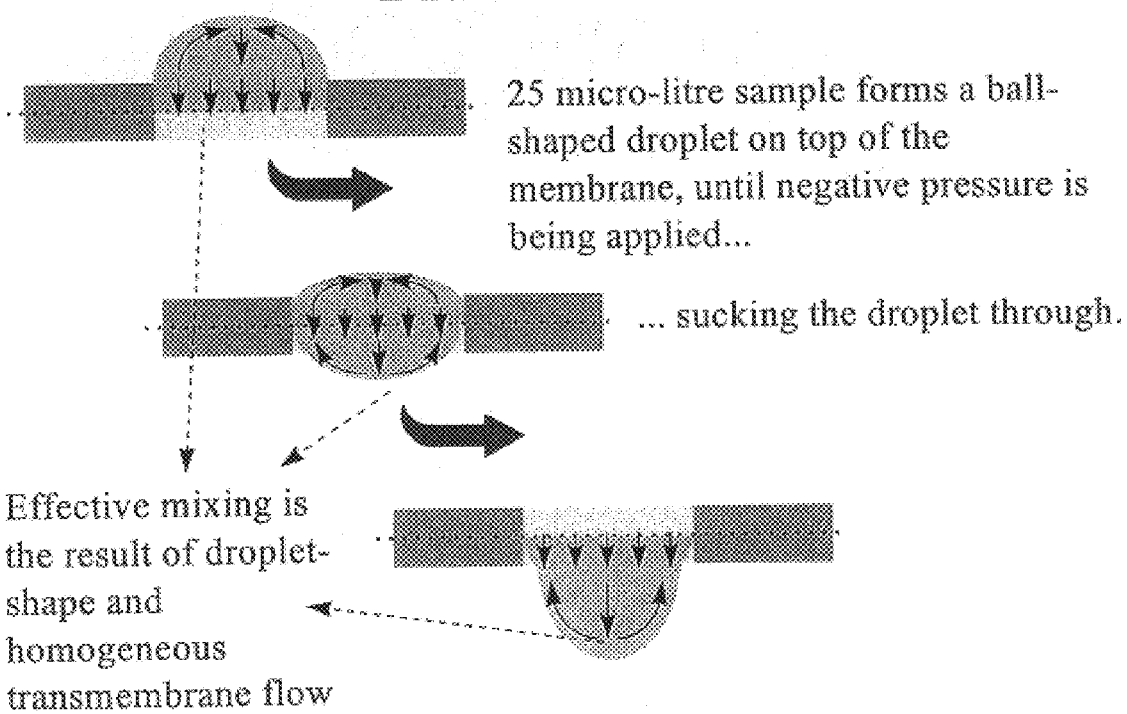
FIG. 1: In this figure it is shown how the fluid forms a ball shaped droplet on top of the membrane, until negative pressure is applied. The droplet is sucked trough the device. Ad a result of droplet shape and the homogeneous flow trough the membrane the fluid is effectively mixed.
Figure 2:
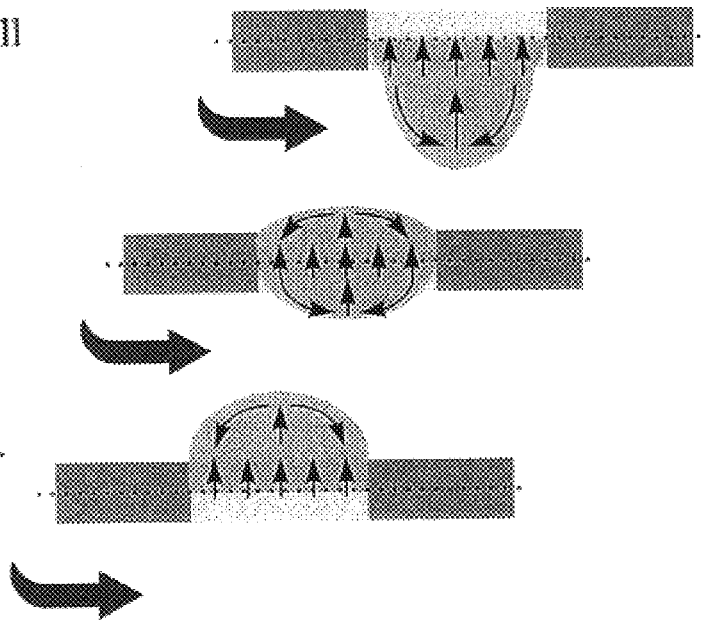
FIG. 2: In this figure it is illustrated how reversing the pressure will reverse the process. Ultimately the droplet is on top of the membrane again.
Figure 3:
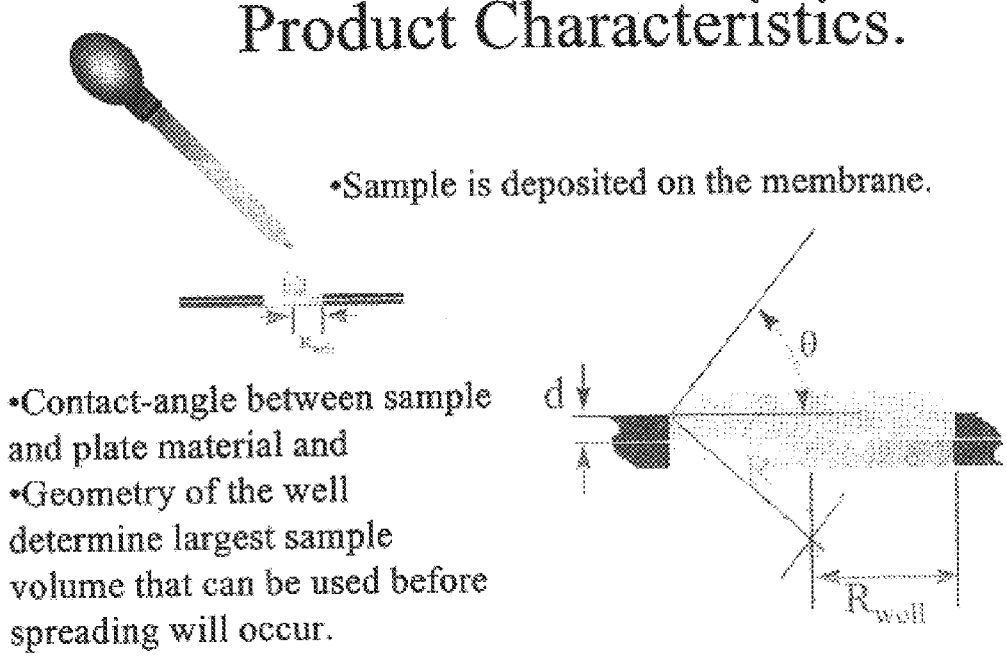
FIG. 3: In this figure the relevant parameters of the device are indicated that determine thelargest droplet size before spreading will occur.
Figure 4:
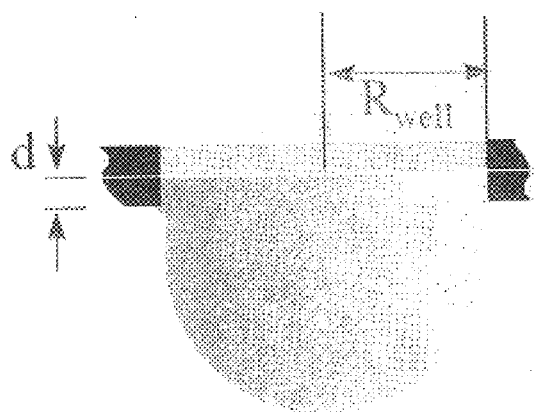
FIG. 4: In this figure the relevant parameters are indicated that determine the largest droplet size before a droplet will fall off the device because of its weight

With the method according to the invention, mixing of the sample fluid is promoted during the performance of the assay, as well as an optimal contact between the sample fluid and the inside of each of the troughgoing channels in which the binding substances are immobilized.

The substrates in the devices have oriented trough going channels which have been provided with one or more binding substances, specific for one or more analytes present in the sample. When a drop of sample liquid is applied to the top surface of the substrate it is intended to pass trough the channels of the substrate, thus contacting the binding substances in the channels.

The channels in the substrate are capillaries and have a very high capillary pressure. Whenever surplus volume on the membrane's surface has been sucked through the capillaries, this capillary pressure will prevent the channels themselves from being emptied. This means that ultimately all flow will stop and that the droplet formed on the other side of the membrane will not be influenced any more by the superimposed pressure difference.

With the present invention it has been found that this effect can be exploited to improve the contact between the sample liquid and the substrate with the binding substances immobilized thereon.

One of the ideas underlying the present invention is to control the sample volume size, or to adjust it to the design parameter of the device (or the other way around) and to benefit from the effects described above to improve the sensitivity and performance of biochemical assays performed with such substrates on which binding substances have been immobilized.

In each biochemical assay there are certain parameters that have to be taken into account when the sample volume used is to be determined. Of course, a volume of sample, being positive for a certain analyte, should comprise enough analyte to generate a detectable signal in an assay. When the expected concentration of a certain analyte is very low, larger quantities of the sample liquid are needed, unless other measures are being taken (e.g. concentration of the sample liquid, amplification of the signal, or for example, when nucleic acid is to be detected, exponentially increasing the amount of "target sequence" in the sample by way of a nucleic acid amplification technique).

On the other hand, sample volumes should not be too small as well. If the binding substance is immobilized on a surface, than the sample volume should be big enough the be able to wet the complete surface or at least ensure a good contact between the surface and the volume. Thus, for most biochemical assays there are more or less standard sample volumes.

With the method of the invention a device may be used that comprises one or more round wells with a fixed diameter. In each well the substrate having oriented trough going channels is exposed, and the area of the substrate exposed in the well is provided with at least one binding substance specific for at least one of said analytes.

Many of the round wells may be provided in one plate, for example by placing the substrate between a top cover and a bottom cover, whereby the wells are formed by holes made on the same location in both the top cover and bottom cover (see FIG. 1). The volume of liquid that is placed in each well to perform the assay can be optimized based on the characteristics of both the sample fluid and the membrane.

With the method of the invention the sample volume size may be adjusted, based on the design parameters of the device and the substrate in particular: the sample volume should not exceed a certain maximum value. Sample volumes, applied to a certain well of the device, that exceed the maximum value will fall off the substrate due to the weight of the fluid.

However, a volume of sample fluid with a weight below the maximum value will stay attached to the lower surface of the substrate due to the surface tension of the fluid. When samples with a volume below this maximum value are used, this enables a far more efficient use of the substrate.

A volume that stays attached to the lower surface can be contacted with the interior surface of the channels in the substrate again, by generating a reverse flow trough the substrate, till the complete volume of sample fluid is back in its original position: on the top surface of the substrate where it had been applied.

The procedure can be repeated and a alternating flow trough the substrate can be generated as often as necessary, ensuring an optimal contact between the sample fluid and the interior surface of the substrate where most of the binding substances are located.

Preferably the volume of the sample fluid is controlled so that it will not be falling of the substrate by its weight.

This puts certain restrains on the maximum volume sample that can be handled by a device with certain dimensions. So, if a certain sample volume is absolutely necessary to be able to perform an assay, than the dimensions of the substrate and the device may be adjusted accordingly (to prevent the use of a sample volume that will fall trough the device due to its weight). If the sample volume is not critical, a device with fixed dimensions can be used and the sample volume may be adjusted to the dimensions of the device. In either way, the dimensions of the device and the substrate should "match" the sample volume and other characteristics of the sample fluid. The maximum volume that will remain attached to the surface when it has passed trough the capillary channels can be calculated.

The important dimensions here are the fluid characteristics ($\gamma$: surface tension, $\rho$: specific mass, g: gravitational acceleration), the dimensions of the well and the dimensions of the substrate. The relation between the maximum volume that will stay attached to the lower surface of the substrate ($V_{max\ 2}$) and these dimensions is governed by the following equation:

$$V_{max2} = \pi \cdot R_{well} \cdot \left( \frac{2 \cdot \gamma}{\rho \cdot g} + R_{well} \cdot d \right)$$

wherein $R_{well}$ = the radius of a well $d$ = the thickness of the substrate $\partial$ = the contact angle between the sample fluid and the surface of the substrate.

$\gamma$ = the surface tension of the sample liquid $\rho$ = specific mass of the sample liquid $g = 9.8$ m/s$^2$ Thus, to prevent the liquid sample volume for falling of the substrate the sample volume should preferably not exceed $V_{max\ 2}$.

A drop of sample fluid on the surface of the membrane will automatically take a spherical form. The contact angle between the surface and the liquid is characteristic for the material and will always be less than 90 degrees. The spherical drop that has formed will immediately be drawn into the capillary channels of the substrate with a speed that is determined by the dimensions of the capillary channels and the contact angle with the substrate.

The method of the invention also results in better mixing of the sample volume. It has been found that effective mixing is the result of droplet shape and homogenous flow trough the substrate.

In a preferred embodiment of the invention the sample volume and parameters of the device are adjusted to exploit this effect and to maximize the mixing of the fluid. Thus any analyte present in the sample will ultimately be contacted with the binding substances immobilized on the substrate.

The mixing effect of the pressure difference on the sample volume is related to the shape of the surface of the liquid in a well of the device.

Preferably sample volumes are used that will form a drop with a sphere-like surface on the well.

To ensure the improved mixing effect an efficient sample volume should be chosen. When the sample volume is to high, the well will overflow and the drop shape of the sample volume will be disturbed or the sample will end up in other wells, in either way, it cannot be ensured that the same sample fluid is pumped trough the channels of the substrate in one specific well anymore. The volume of the sample is also influenced by the further dimensions of the well. A well in the device will have certain depth and radius. Thus, where one would like to keep a certain sample volume restricted to a particular well, the dimensions of the well have to be taken into account when the sample volume is calculated. Or, again, if a certain sample volume is required for a particular assay, the dimensions of the well will have to be adjusted according to the required sample volume.

The contact angle between the sample and the material of the device and the geometry of the well determine the largest sample volume that can be used before spreading will occur. The relationship between this largest sample volume is ($V_{max}$) and the other parameters is governed by the following equation:

$$V_{max} = \pi \cdot R_{well}^2 \cdot \left( d + \frac{R_{well}}{3 \cdot \sin^3 \vartheta} (1 - \cos \vartheta)^2 (2 + \cos \vartheta) \right)$$

wherein:

$R_{well}$ = the radius of the well d = the thickness of the substrate $\partial$ = the contact angle between the sample fluid and the surface of the substrate.

In a preferred embodiment of the invention a sample volume is used that fulfills all requirements listed above. Thus, it does not exceed $V_{max2}$ to make sure that the drop of sample fluid will not fall of the device at the lower surface. The sample fluid should also not exceed $V_{max}$ to make sure that the wells of the device do not overflow when the sample is applied. Thus, the sample volume should most preferably not exceed the lower value of $V_{max2}$ and $V_{max}$.

The sample volume can flow trough the substrate under influence of a pressure difference. The flow trough the substrate is homogeneous. Because of the very high capillary pressure of the channels (capillaries) in the substrate, the flow will automatically stop when there is no more sample left on the upper surface of the substrate.

The capillary pressure of the substrate in a well will usually be much higher than the pressure difference that is applied to generate the flow. Thus, it is virtually impossible to "push the fluid from the substrate" by applying a pressure difference that is to high. The flow trough the substrate should be optimized according to the assay that is performed. Of course the flow should be such that it allows the binding of an analyte to the binding substance.

Washing of the membrane can, for example, be performed by applying multiple droplets of washing liquid on top of the substrate in a well under constant pressure over the substrate. Because of the homogeneous flow all parts of the substrate will be washed equally well.

When the accumulated volume of the droplets exceeds $V_{max2}$ the wash fluid will fall off. To remove attached droplets at the end of the washing step, for example, a special shaped hydrophilic counterplate may be used.

Furthermore the present invention provides devices with substrates having oriented trough going channels, the design and dimensions of which have been optimized for the use with the method of the invention, as well as an apparatus in which the method according to the invention can be performed in an automated way.

A device that can be used with the method of the invention preferably comprises one or more round wells with a fixed diameter, exposing a substrate of a specific thickness said substrate having oriented trough going channels, the channels being provided with a first binding substance in at least one area of the substrate wherein the substrate is placed between a top cover and a bottom cover and the wells are formed by holes made on the same location in both the top cover and bottom cover (FIG. 1).

By constructing the device in this way, it is possible to design and fabricate devices that are adjusted to the use of a particular sample volume. The substrate will be exposed in the wells that have been defined by the holes made in the top- and bottom cover. The depth of each well can be chosen by adjusting the thickness of the cover plate. A sample volume can be put in the wells defined by the round holes made in the top cover plate and the contact angle valid for the plate material and the sample fluid. When a pressure difference is applied over the device, the sample volume will be drawn trough the substrate in the wells and will appear as a drop hanging from the substrate in the round opening made in the bottom cover plate.

The material of which the plates are made can be nay material known in the art, for example, the material of which microtiter plates are composed. The material of the plates should not hinder the detection of any signal from the substrate.

The assay results can be read by looking at the surface of the substrate. This can be done in any convenient way known in the art.

The device according to the invention can be used to detect many analytes at the same time. For example, by testing for different analytes in different wells of the device. The device may also be used to screen multiple samples, for example by performing the same assay for a different sample in each well.

Preferably the binding substance bound to the substrate is chosen from the group consisting of a nucleic acid probe, an antibody, an antigen, a receptor, a hapten, and a ligand for a receptor.

Assays in which the device according to the present invention can be used may include sequencing by hybridization, immunoassays, receptor/ligand assays and the like.

When the device is used as a tool to obtain DNA sequence information, a large array of areas is provided, each area comprising as a first binding substance an oligonucleotide probe of a different base-pair sequence. The substrate in each well in the device can be provided with a spotted array each spot comprising a different binding substance. Since one device can have many wells, many arrays could be placed in one device or an array can be divided over different wells.

If a sample containing DNA or RNA fragments with a (partly) unknown sequence is brought into contact with the substrate a specific hybridization pattern may occur, from which pattern the sequence information of the DNA/RNA can be derived. Such "sequencing by hybridization" methods are well known in the art (see e.g. Fodor, S. P. A. et al. (1992), Science 251, 767–773 and Southern, E. M. et al. (1994) Nucleic Acids Res. 22, 1368–1373).

The device according to the present invention may also be used to screen a biological specimen, such as blood, for a large number of analytes. The array may consist of areas comprising oligonucleotide probes specific for, for example, *E. coli, S. aureus. S. pneumoniae* etc. A biological sample can be prepared as described in EP 0.389.063. If this sample is brought into contact with the substrate, the resulting hybridization pattern can be read e.g. using a CCD camera in combination with an appropriate optical marker.

Apart from screening for bacteria, the device is suitable for the detection of viruses, as well as the classification of different subtypes of, for example, HIV- and HCV viruses, etc. Virus classification may be essential to determine potential drug resistance. In general it requires the ability to detect single point mutations in the virus RNA.

The device is also suited for performing sandwich immunoassays. In that case, it is preferred that a second antibody is used for binding to bound analyte, said second antibody for each of the analyte being recognized by a third labeled antibody. This may be achieved if the second and third antibodies are derived from different species and the third antibody is raised against antibodies of the other species. Thus it is avoided to label the second antibody for each particular analyte.

The device is also suited for performing "pepscans" as disclosed in Geysen et al., Proc. Natl. Acad. Sci. USA 81:3998–4002 (1984). In that case the first binding substances that are attached to the different areas of the substrate constitute different sequences of amino acids. If the substrate is brought into contact with a liquid that contains a particular analyte, a reaction pattern may occur representing the specific affinity of the analyte for the different amino acid sequences.

It is preferred that the binding substance is covalently bound to the substrate. This minimizes loss of the binding substance from the substrate. Covalent binding of an organic compound to a metal oxide is well known in the art, for example using the method described by Chu. C. W., et al. (J. Adhesion Sci. Technol., 7, pp.417–433, 1993) and Fadda, M. B. et al. (Biotechnology and Applied Biochemistry, 16, pp. 221–227, 1992).

The substrate is preferably an electrochemically manufactured metal oxide membrane, preferably composed of aluminium oxide. Such membranes are described in co-pending application number EP98/04938.

The present invention further relates to an apparatus to perform the method of the invention.

An apparatus according to the invention comprises:
  means for the addition of a controlled amount of a fluid to at least one of the wells of the device,
  means for applying and/or maintaining for a sufficient amount of time a controlled pressure difference over the substrate in each of the wells.

Preferably the apparatus would also comprise means to control the temperature around the device. Thus the device may be equipped with an incubator in which the device is placed to ensure a constant temperature in each well. Thus, an apparatus according to the invention would allow the controlled addition of sample fluid to the wells. As a means to apply the sample fluid to the wells the apparatus could comprise a pipettor that can be moved over the substrate to add fluid to different respective wells. The apparatus may comprise one pipettor that is movable and can be directed to different wells, or a different one for each well in particular. The means for applying the fluid may be connected to sample fluid reservoirs and washing fluid reservoirs or the like. The apparatus should be constructed in such a way that the amount of fluid added to each well can be controlled and can be adjusted. Preferably the apparatus comprises the necessary programmable controllers to be able to feed the apparatus with the relevant parameters on the basis of which the programmable controller can calculate the matching sample volume.

The apparatus also comprises means to apply a pressure difference over the device. The pressure difference may also be regulated by a programmable unit.

Thus, the whole apparatus may be automated and perform the assay with the right pressure difference and amounts of sample fluid, once it is provided with the necessary input such as details about the sample and the substrate.

To be able to apply a pressure difference over the device, it may be placed as a cover over a container. The means for applying a pressure difference will in that case operate by changing the pressure in the container.

Conveniently the container is connected to a fluid outlet that can be opened and closed, and trough which any liquid can be removed from the container.

The apparatus is preferably equipped with a reader capable of reading a signal from the (top) surface of the substrate in each of the wells.

The reader may read a signal when the complete assay has been performed but it may also be used to register the growth of the signal while the assay is performed. In that case the reaction between the analyte and the binding substance may be continuously monitored during the alteration of the flow trough the substrate by reading the signal from the top surface of the membrane whenever the fluid has passed trough the substrate and hangs as a drop underneath the substrate.

We claim:

1. A method for analyzing one or more fluid samples for the presence, amount or identity of one or more analytes present in said samples, comprising the steps of:
   (a) providing a device comprising one or more round wells with a fixed diameter, said wells exposing a substrate having a thickness, said substrate having oriented through going channels, and an area of the substrate exposed in the well being provided with at least one binding substance specific for at least one of said analytes;
   (b) adding an amount of sample fluid to one or more of the wells of the device;
   (c) generating an alternating flow through the substrate in the wells by applying an alternating pressure difference over the substrate in the wells, said alternating pressure difference being lower than a capillary pressure of the channels in the substrate, whereby a liquid volume of the sample is forced to pass through the channels in the substrate from an upper side of the substrate to a lower side of the substrate and back at least one time, so as to allow for a reaction between analyte present in the sample and the binding substance(s);
   (d) reading any signal generated in any of the wells; and
   (e) determining from said signal(s) the presence, amount and/or identity of said one or more analytes.

2. The method according to claim 1, wherein the substrate is washed prior to reading the signal.

3. The method according to claim 1, wherein the amount of added sample fluid is calculated on the basis of at least one of a dimension or a material characteristic of the wells, the substrate and the sample fluid.

4. The method according to claim 3, wherein the amount of sample fluid added to each well does not exceed $V_{max2}$, and $V_{max2}$ is calculated according to the following equation:

$$V_{max2} = \pi \cdot R_{well} \cdot \left(\frac{2 \cdot \gamma}{\rho \cdot g} + R_{well} \cdot d\right)$$

wherein $R_{well}$=a radius of the well d=a depth of the well

γ=a surface tension of the sample liquid

ρ=specific mass of the sample liquid g=gravitational acceleration.

5. The method according to claim 4, wherein a volume of the sample does not exceed the smallest value of $V_{max2}$.

6. The method according to claim 1, wherein the amount of sample fluid added to each well does not exceed $V_{max}$, and $V_{max}$ is calculated according to the following equation:

$$V_{max} = \pi \cdot R_{well}^2 \cdot \left(d + \frac{R_{well}}{3 \cdot \sin^3\vartheta}(1 - \cos\vartheta)^2(2 + \cos\vartheta)\right)$$

wherein $R_{well}$=a radius of the well d=a depth of the well

∂=a contact angle between the sample fluid and a surface of the substrate.

7. The method according to claims 6, wherein a volume of the sample does not exceed the smallest value of $V_{max}$.

8. The method according to claim 1, whereby a downward flow through the channels of the substrate is created by applying an underpressure underneath the device, and said underpressure is maintained until all sample fluid has passed through the channels of the substrate and has formed a drop that hangs underneath the substrate of the well, then an upward flow through the channels of the substrate is created by raising the underpressure to a sufficient overpressure, and said overpressure is maintained until all fluid has passed through the channels again in an upward direction and has formed a drop on an upper surface of the substrate, and repeating these steps for as many times as necessary to assure an optimal contact between the analyte(s) and the binding substances).

9. The method according to claim 1, wherein the reaction between the analyte and the binding substance is continuously monitored during alternation of the flow through the substrate by reading the signal from a top surface of the substrate.

10. The method according to claim 9, wherein the signal is read whenever the fluid has passed through the substrate and hangs as a drop underneath the substrate.

11. The method of claim 1, wherein the channels of the substrate are provided with a first binding substance in at least one area of the substrate, wherein the substrate is placed between a top cover and a bottom cover and the wells are formed by holes made on corresponding locations in both the top cover and bottom cover.

12. The method according to claim 11, which is preformed with an apparatus for the automated performance for one or more assays, and which comprises (a) means for addition of a controlled amount of a fluid to at least one of the wells of the device; and (b) means for applying and/or maintaining for a sufficient amount of time a controlled pressure difference over the substrate in each of the wells.

* * * * *